(12) United States Patent
Nevitt

(10) Patent No.: US 10,596,486 B2
(45) Date of Patent: Mar. 24, 2020

(54) PLANT MATTER FRACTIONAL DISTILLATION SYSTEM USING HEATED AIR INDUCTION INTO PRECISELY HEATED CHAMBER TO EXTRACT A PLANT'S ORGANIC COMPOUNDS WITHOUT USE OF SOLVENTS

(71) Applicant: Louis Phillip Nevitt, Long Beach, CA (US)

(72) Inventor: Louis Phillip Nevitt, Long Beach, CA (US)

( * ) Notice: Subject to any disclaimer, the term of this patent is extended or adjusted under 35 U.S.C. 154(b) by 0 days.

(21) Appl. No.: 16/137,463

(22) Filed: Sep. 20, 2018

(65) Prior Publication Data

US 2019/0083902 A1 Mar. 21, 2019

Related U.S. Application Data

(60) Provisional application No. 62/561,437, filed on Sep. 21, 2017.

(51) Int. Cl.
| | |
|---|---|
| *B01D 3/34* | (2006.01) |
| *B01D 11/02* | (2006.01) |
| *C07C 39/21* | (2006.01) |
| *C07D 311/92* | (2006.01) |
| *C07D 311/80* | (2006.01) |
| *C07C 37/00* | (2006.01) |
| *B01D 11/00* | (2006.01) |

(52) U.S. Cl.
CPC .......... *B01D 11/0257* (2013.01); *B01D 3/343* (2013.01); *C07C 37/004* (2013.01); *C07C 39/21* (2013.01); *C07D 311/80* (2013.01); *C07D 311/92* (2013.01); *B01D 2011/007* (2013.01)

(58) Field of Classification Search
CPC ...... B01D 3/34; B01D 3/343; B01D 11/0257; C07C 39/21; C07D 311/92
See application file for complete search history.

(56) References Cited

U.S. PATENT DOCUMENTS

| | | | | |
|---|---|---|---|---|
| 4,257,945 | A * | 3/1981 | Martel ............... | B01D 11/0207 202/169 |
| 5,235,992 | A * | 8/1993 | Sensabaugh, Jr. ... | A24B 15/165 131/194 |
| 8,329,229 | B2 * | 12/2012 | Gonzalez ............. | C11B 9/027 424/725 |
| 8,846,409 | B2 * | 9/2014 | Flockhart ............ | C07D 311/80 436/172 |
| 10,159,908 | B2 * | 12/2018 | Thomas ............... | B01D 1/14 |
| 2004/0147767 | A1 * | 7/2004 | Whittle .............. | B01D 11/0242 549/390 |
| 2008/0128260 | A1 * | 6/2008 | Balass ................ | B01D 5/0012 202/176 |
| 2014/0001027 | A1 * | 1/2014 | Balass ................ | B01D 3/38 203/1 |
| 2016/0228787 | A1 * | 8/2016 | Payack ............... | B01D 3/10 |

(Continued)

*Primary Examiner* — Jonathan Miller
(74) *Attorney, Agent, or Firm* — PATNSTR, APC; Tom Brody; Peter Jon Gluck, Esq.

(57) ABSTRACT

The present disclosure provides a system for extracting terpenes and cannabinoids from plant matter without use of volatile solvents and without use of lipids as solvents. The system uses heated air, drawn through plant matter for volatilizing desired compounds, where the air is at a predetermined temperature, followed by collecting the desired compounds in a condenser.

21 Claims, 2 Drawing Sheets

(56) References Cited

U.S. PATENT DOCUMENTS

Figure 1:
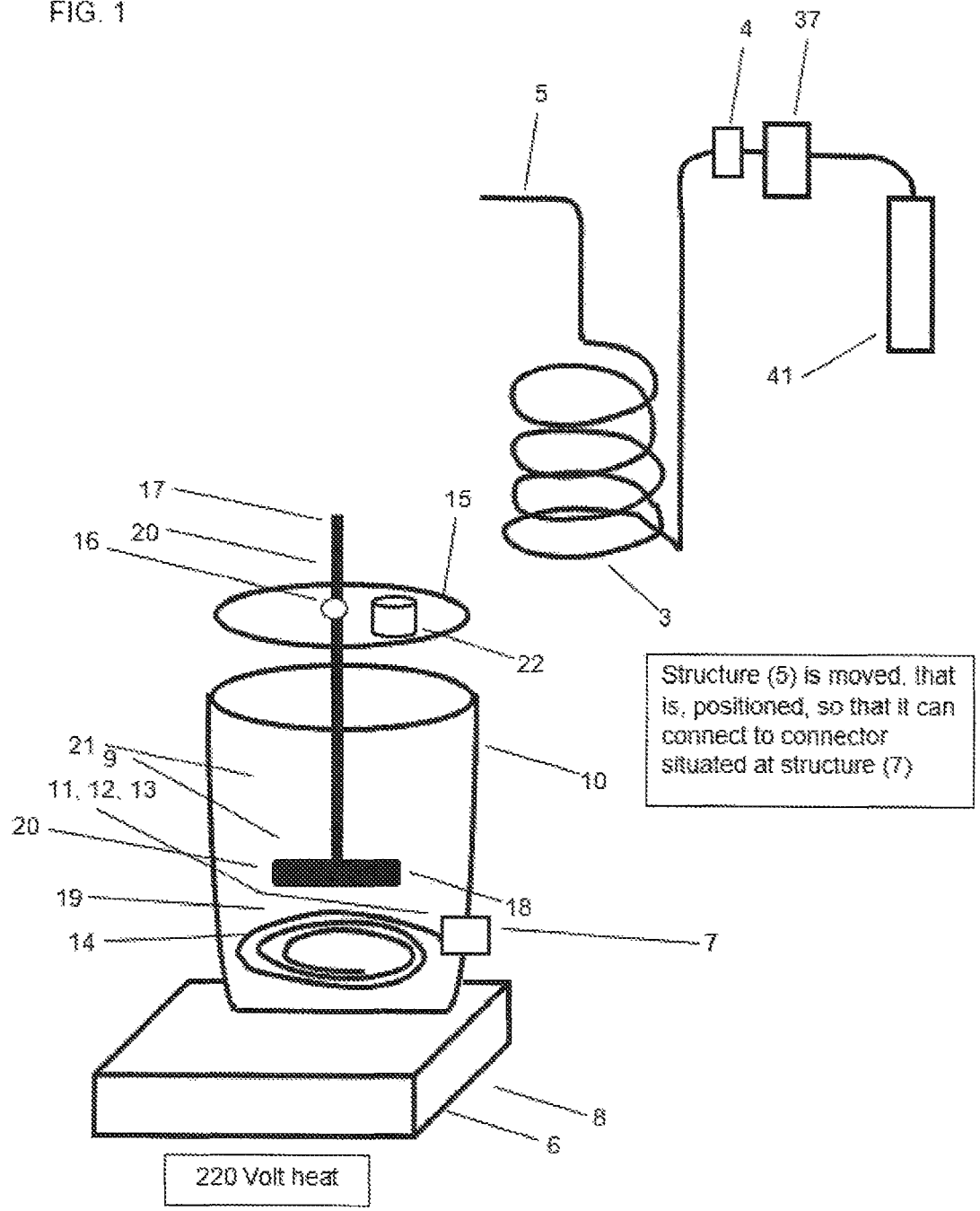

2016/0250564 A1* 9/2016 Thomas .................. B01D 1/14
554/8
2019/0151771 A1* 5/2019 Thomas .................. B01D 1/14

* cited by examiner

PLANT MATTER FRACTIONAL DISTILLATION SYSTEM USING HEATED AIR INDUCTION INTO PRECISELY HEATED CHAMBER TO EXTRACT A PLANT'S ORGANIC COMPOUNDS WITHOUT USE OF SOLVENTS

CROSS REFERENCE TO RELATED CASES

This Application claims the benefit of, and priority to, U.S. Provisional Patent Application Ser. No. 62/561,437 filed Sep. 21, 2018, the content of which is incorporated herein by reference herein in its entirety.

FIELD OF THE DISCLOSURE

The disclosure relates to systems and methods for removing and collecting terpenes from heated plant matter.

BACKGROUND OF THE INVENTION

This present disclosure relates to ways of extracting cannabinoids and terpenes from plant substrates using a heated chamber with a flow of heated air drawn with a pump.

Extraction of cannabis and hemp can be done via many methods, using various of FDA-approved food grade solvents. The most commonly used solvents are hydrocarbons such as hexane, pentane, butane or propane. In addition to these hydrocarbon solvents, lipid-based solvents such as canola oil, soybean oil, olive oil, flax seed oil, hemp oil are used in cannabis extraction methods. Supercritical carbon dioxide is also used in cannabis extraction, but the expensive machinery and the post-extraction steps required to purify a supercritical fluid extraction (SFE) extract of undesired plant lipids, makes SFE the least desirable method for any commercial processor.

Drawbacks of hydrocarbon extraction methods include the volatility of hydrocarbon solvents, the risk of fires and explosions, and the cost associated with fitting a laboratory with explosion proof electronics and ventilation fans. Another problem relating to hydrocarbon solvents is toxicity and burns. For example, butane is used as a solvent to extract tetrahydrocannabinol (THC) from cannabis plants. During extraction, the flammable and volatile butane gas permeates the air and can be easily ignited through static electricity or by a flame (see, Bell, Slim, Monte (2015) J. Med. Toxicol. 11:422-425). Moreover, butane be toxic when inhaled (see, Sironi, Amadasi (2016) Forensic Sci. Int. 266:e52-e58; Sugie, Sasaki (2004) Forensic Sci. Int. 143:211-214). Existing solvent-based methods use butane, propane, carbon dioxide, alcohol, ethanol, or bonding agents. The present disclosure can exclude any of these chemicals.

The systems, apparatus, and methods of the present disclosure provide advantages that satisfy unmet needs. The present disclosure eliminates the need for solvents and liquid distillation equipment, by distilling oils out of plant matter directly. The system and compositions of the present disclosure provides medicinal compositions that are free of any residual solvents. Also, the system and compositions of the present disclosure avoid cumbersome and expensive equipment and methods that require freezing or ultra-low temperature during extraction.

SUMMARY OF THE DISCLOSURE

In brief, the present disclosure provides a system for extracting and purifying chemicals from plant matter, wherein the extracting uses a flow of heated air to volatilized chemicals from plant matter, and wherein the extracting does not use any added solvent to extract chemicals from the plant matter, and wherein the purifying comprises a condenser that condenses at least a portion of the volatilized chemicals, the system comprising: (a) A source of inert gas, (b) A heat chamber vessel that comprises an interior chamber region, an inside wall that defines the interior chamber region, an outside wall, a base, an upper region of the interior chamber region, wherein the upper region is capable of receiving and supporting a heat chamber vessel lid, and wherein the base of the heat chamber vessel is operably linked to a source of heated inert gas, (c) A conduit for transmitting the inert gas to the heat chamber vessel, (d) A screen that is capable of supporting plant matter and capable of allowing a flow of heated air directly against at least a portion of the supported plant matter, (e) A rotator arm that is operably linked with a stirring rod, wherein the rotator arm is capable of agitating any plant matter that is supported by the screen, (f) A distillation tube comprising a proximal terminus and a distal terminus, wherein the proximal terminus is capable of receiving a vapor arriving from heat chamber vessel, and wherein the distillation tube is capable of at least partially condensing the vapor to produce a fluid, wherein the proximal terminus of distillation tube is operably linked with the heat chamber vessel, and wherein the distal terminus of distillation tube is operably linked with one or more collecting flasks, (g) One or more collecting flasks that are operably linked with the distillation tube, wherein the one or more collecting flasks is capable of receiving and storing the fluid, (h) At least one source of heat, wherein the at least one source of heat comprises one, two, or all three of: (1) A heat air induction system that is capable of heating inert gas leaving said source of inert gas, (2) A radiant heat source or hot plate that is situated under the heat chamber vessel and capable of transmitting heat to said interior chamber region, and (3) A heating blanket that is wrapped around the heat chamber vessel, and capable of transmitting heat to said interior chamber region.

In another aspect, the present disclosure provides the above system, further comprising a heating vessel lid that is capable of air-tight sealing of the heat chamber vessel, and that when engaged in air-tight sealing of the heat chamber vessel is capable of being removed from physical contact with the heat chamber vessel thereby allowing deposit of plant matter on said screen or allowing removal of plant matter from said screen. Moreover, what is provided is the above system, further comprising a heating vessel lid, wherein the heating vessel lid comprises a distillation hole, and wherein the distillation hole is capable of allowing passage of a vapor from the heat chamber vessel to the distillation tube. What is also embraced is the above system, wherein said conduit for transmitting an inert gas to the heat chamber vessel comprises a tube, hose, pipe, or duct.

In exclusionary embodiments, the present disclosure provides the above system that does not comprise any solvent, excluding consideration of any naturally occurring solvent that may be comprised by the plant matter. In further exclusionary embodiments, the present disclosure provides the above system that does not comprise any solvent, excluding consideration of any naturally occurring solvent that may be comprised by the plant matter, wherein the excluded solvent is one or more of ethanol, benzene, acetone, propanol, isopropanol. In additional exclusionary embodiments, the present disclosure provides the above system that does not comprise any vegetable oil, excluding consideration of any naturally occurring vegetable oil that may be comprised by the plant matter. Also, what is provided is the above system that does not comprise any vegetable oil, excluding consideration of any naturally occurring vegetable oil that may be comprised by the plant matter, wherein the vegetable oil is one or more of soy oil cottonseed oil, peanut oil, corn oil, safflower oil, or sunflower oil.

Regarding plant matter, the present disclosure provides the above system that comprises plant matter, and wherein at least some of the plant matter is supported by the screen, or wherein at least 50% of all of the plant matter is supported by the screen (e.g., sitting on the screen), or wherein at least 60%, at least 70%, at least 80%, at least 90%, at least 95%, at least 98%, or essentially 100%, is supported by the screen. The percentage values are with regard to the total amount of plant matter inside heat chamber vessel.

In another plant matter embodiment, what is provided is the above system that comprises plant matter, and wherein at least some of the plant matter is supported by the screen, and wherein the plant matter comprises cannabis sativa.

Also provided is the above system that is capable of vaporizing terpenes and cannabinoids from plant matter at a temperature that is lower than the temperature that is needed to initiate combustion of the plant matter. Also embraced is the above system that is capable of heating the inert gas prior to passage of the inert gas into the heat chamber vessel, thereby preventing the inert gas from cooling the atmosphere inside heat chamber vessel. Further embraced is the above system, wherein the heat chamber vessel comprises an interior atmosphere, wherein the system is capable of heating the inert gas prior to passage of the inert gas into the heat chamber vessel, thereby preventing the inert gas from cooling the atmosphere inside the heat chamber vessel.

In an embodiment relating to the atmospheric pressure within heat chamber vessel, what is provided is the above system, wherein the heat chamber vessel interior has an atmospheric pressure, and wherein the atmospheric pressure is maintained at or below 760 millimeters of mercury. This value (760 millimeters) is the atmospheric pressure in a typical laboratory that is situated at sea level.

In methods embodiments, what is provided is a method for extracting and purifying chemicals from plant matter, the method comprising the steps of: (i) Providing a flow of a heated inert gas to a heat chamber vessel, wherein the heat chamber vessel is closed to an external environment by a lid that comprises a distillation hole, wherein the heat chamber comprises a base region that comprises an inlet, an upper region, and a screen, wherein the heated inert gas is introduced at the inlet in the base region, wherein the screen is situated above the base region and below the upper region and wherein plant matter is residing on or dispersed on the screen, (ii) Allowing the flow of heated inert gas to rise from the base region and pass through the screen, and pass through the plant matter, thereby extracting and volatilizing volatile chemicals from the plant matter, resulting in a chemical-rich vapor, (iii) Drawing the chemical-rich vapor through the distillation hole, wherein the distillation hole is operably linked with a distillation tube, wherein the distillation tube capable of being cooled with cold water, (iv) Cooling the distillation tube with the cold water, thereby condensing at least some of the chemicals in the chemical-rich vapor, and (v) Collecting the condensed chemicals in at least one collecting flask, wherein the method does not involve any contacting of a liquid solvent with the plant matter, does not involve any contacting of a vegetable oil with the plant matter, does not involve any extracting of chemicals from the plant matter with a liquid solvent, and does not involve any extracting of chemicals from the plant matter with any vegetable oil.

In another methods embodiment, what is provided is the above method wherein the plant matter is cannabis sativa, and the above method wherein the volatile chemicals from the plant matter comprise terpenes and cannabinoids.

In an agitating embodiment, what is provided is the above method, further comprising agitating the plant matter with a rotator arm, wherein the rotator arm is operably linked to a stirring rod, further comprising driving the stirring rod with angular momentum, either manually or with a motor, thereby resulting in rotation of the rotator arm.

In a methods embodiment relating to steps of heating, what is provided is the above method, wherein the heat chamber vessel comprises a base, further comprising: (1) Heating the heat chamber vessel with a heating blanket, (2) Heating the heat chamber vessel with a radiant heat source or hot plate, and (3) Heating the inert gas to produce a heated inert gas, wherein the heated inert gas is introduced at the base of the heat chamber vessel, and wherein the heating of the inert gas is sufficient to prevent the introduced heated inert gas from cooling down the heat chamber vessel.

In a methods embodiment relating to analysis of product collected in one or more collecting flasks, what is provided is the above method, further comprising analyzing the collected condensed chemicals, and quantifying and identifying any terpenes and cannabinoids.

In a methods embodiment that determines success in purification, what is provided is the above method, that results in a Degree of Purification Factor of at least 1.5, where the Degree of Purification Factor is calculated by quantitative analysis of the sum of at least 90% of all terpenes and by quantitative analysis of the sum of at least 90% of all waxes, and where quantitative analysis is performed on the starting material (plant matter) and on the product (composition in collection flask). This method can include the step of analyzing starting material (plant matter), the step of analyzing substances or compositions in one or more or all collecting flasks, and the step of making calculations for determining Degree of Purification.

BRIEF DESCRIPTIONS OF THE DRAWINGS

FIG. 1. VOLATILIZING CHEMICALS. Heat from radiant heat source (8) passes through screen (19) that holds or supports plant matter. Chemicals, such as terpenes and cannabinoids, that get volatilized by the heat, are swept upwards by flow of heated inert gas, and pass through distillation hole (22). Interior of heat chamber (10) is healed by copper coil heated air tube (3) and heating blanket (9). Tank (41) is optionally used as the source of inert gas. Stirring rod (17) can have a loop on top for grabbing by the hand to ensure more thorough mixing. A hand drill can be attached to stirring rod, instead of stirring by hand. The system shown in FIG. 1 can be used for processing and stirring, for example, from two pounds of plant matter to about 50 pounds of plant matter. Screen (19) has three functions: to diffuse heated air from coil, to keep plant matter out of coil and off of bottom of heat chamber vessel and, to keep agitator paddle off of coil. The screen (19) is situated on top of the copper coil, and both the screen and the copper coil are located inside of the heat chamber vessel (10).

Figure 2:
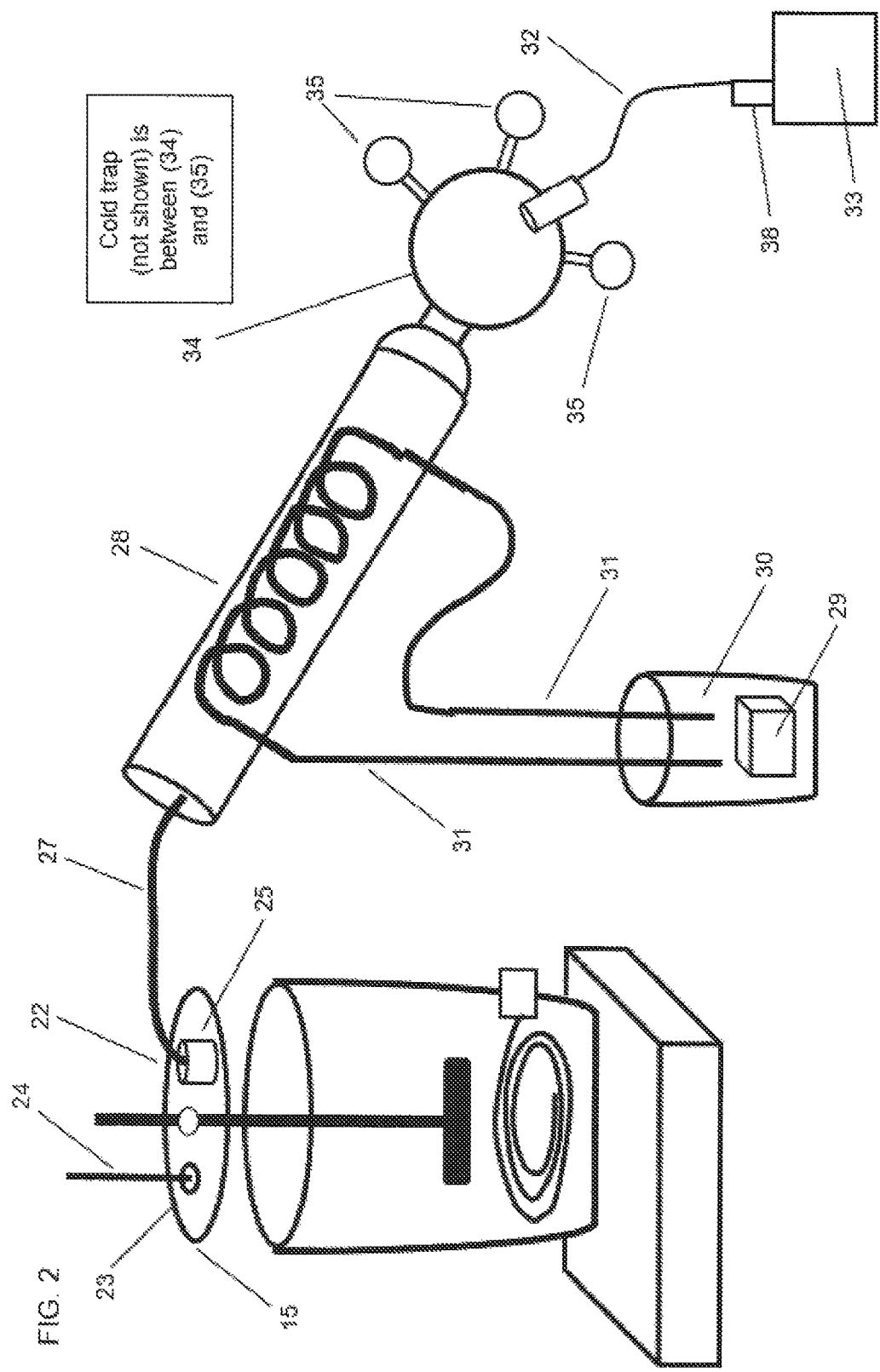

FIG. 2 CONDENSING AND COLLECTING CHEMICALS. The screen, heat chamber vessel, and associated structures from FIG. 1 are also shown in FIG. 2. FIG. 2 discloses tube connector (27) that brings volatilized chemicals from heating chamber into distillation tube (28). Distillation tube gets cooled from cold water that enters and exists through water tubing (31). Water tubing (31) encompasses a region that enters distillation tube (28) and a region that exits distillation rube (28). Cold trap (42) (not shown in FIG. 2) further condenses chemical, ensuring maximal condensation, and condensed chemicals are collected in collecting flasks (35). Location of cold trap is between (34) and (35).

DETAILED DESCRIPTION

As used herein, including the appended claims, the singular forms of words such as "a," "an," and "the" include their corresponding plural references unless the context clearly dictates otherwise. All references cited herein are incorporated by reference to the same extent as if each individual patent, and published patent application, as well as figures, drawings, sequence listings, compact discs, and the like, was specifically and individually indicated to be incorporated by reference.

"Derived" as in the phrase, "plant matter that is derived from a given plant," can refer to plant matter that is derived by one or more of harvesting, chopping, drying, grinding, slicing, folding, dedicating, cleaning, washing, any combination thereof, and so on.

The present disclosure minimizes the problem of extracting unwanted materials from plant matter, such as chloroform, lipids, waxes, and pesticides. The present disclosure minimizes these problems by pulling targeted plant compounds based on their boiling point.

The precisely controlled temperature in the heating chamber of the present disclosure allows "cracking" the plant material compounds that vaporize at lower temperatures than needed to combust the plant material. The air induction system of the present disclosure matches the chamber temperature so that the air driving the vaporized compounds to the condensers does not cool the chamber, but instead, increases efficiency of pulling compound materials from the plant material. The vacuum pump of the present disclosure draws the vaporized compounds into the distillation tube, which condenses them back into liquid form. All the while, the mixing system increases the amount of compounds released by aerating the gases released by the plant up to the condensers and evenly spreading the controlled heat.

The present disclosure uses temperature-regulated air induction to precisely control temperature of heating chamber, to allow for solvent-free distillation of plant material.

The scale of the working model of the present disclosure is in the range of about ten/one to about twenty/one, with an industrial machine being able to process 100-200 pounds of dried plant material at a time in 1,000-2,000 gallon, controlled heat cooking vats and kettlers. The working model can be used for in home use on a small scale. For industrial scale, precisely controlled heated and agitated kettles and cookers could be engineered based on our scale design to maintain vacuum not pressure as is normally the case with this type of industrial equipment.

The system and methods of the present disclosure uses glass condensers connected around the kettlelid, going into single or multiple glass globes that capture the oil as it condenses through multiple cooled condensers. The present disclosure also includes a controlled air heating device, as well as hot air induction system.

The system and methods of the present disclosure are advantageous over existing systems and methods for extracting and distilling, but these existing methods use hundreds or even thousands of pounds of pressure per square inch, pulling out more plant-derived chemicals that are desired. Because existing systems and methods pull out more plant-derived chemicals than desired, in terms of quantity of chemicals and in terms of the variety of different chemical, existing methods require post-extraction purification methods, such as purification methods that involve chromatography or distillation. The present system and methods reduces the pulling out of undesired substances from plant matter.

The system of the present disclosure can produced a variety of organic compounds, extracted from or derived from plant matter. The system can produce oil compositions having one or the other chemical profiles, where different chemical profiles can be produced by changing the temperatures that the operator uses to vaporize plant compound.

A non-limiting meaning of the term "chemical profile" can be determined by its use. For example, Rauter et al discloses that the term "chemical profile" as it was applied to a plant from Madeira, involved the identification of thirty four flavones, for the identification of the plant's "flavoid profile" (Rauter et al (2009) J. Ethnopharmacology. 122: 384-393). The Rauter reference used the technique of liquid chromatography and electrospray ionization to obtain the "flavoid profile." In addition, Giomaro et al discloses that, "chromatographic profiles of each extract were similar . . . [i]n FIG. 1 is reported the HPLC/DAD chromatogram . . . [d]ata concerning the identification of the peaks are shown in Table 1" Giomaro et al (2014) Chemistry Central J. 8:45 (10 pages). A view of FIG. 1 and of Table 1 reveals eighteen compounds from the HPLC chromatogram, though a few extremely tiny peaks in the chromatogram were not included as numbered compounds. Thus, one meaning of "chemical profile" is a list in a table of compounds, where the numbered compounds in the table is essentially the same, or nearly the same, as the numbered compounds in a chromatogram.

The system of the present disclosure uses a "distillation tube, water cooled" (structure 28) for condensing plant compounds, where the condensed plant compounds pass through a "flask rotating connector" (structure 34), followed by collection in one or more different glass globes (collecting flasks, structure 35). A single glass globe (also indicated by structure number 34) can be used or multiple glass globes (35) can be used. The multiple glass globes can be used to capture lower boiling point compounds first, followed by capture of higher boiling point compounds. Sequential capture in a first glass globe, followed by collection in a second glass globe, followed by collection a third glass globe, and the like, with heating at progressively higher temperatures, can be controlled by a valve that controls an aperture in the neck of the glass globe. Sequential generation of volatilized compounds can be by way of stepwise increases in heating temperature or, alternatively, continually progressive increases in heating temperature. For example, stepwise increases can be in increments of 5 degrees C., 10 degrees C., 15 degrees C., 20 degrees C., 25 degrees C., 30 degrees C., 35 degrees C., 40 degrees C., and so on. Heating occurs in "heat chamber vessel" (structure 10). Heat chamber (10) can be large, for example, 12 inches in diameter.

Vacuum versus pressure. In operation, pressure in heat chamber vessel can be maintained at a vacuum. Alternatively, pressure in heat chamber vessel cars be preventing from rising too far above atmospheric pressure. The goal of preventing pressure of atmosphere from rising too high is to avoid release of undesired volatile chemicals from plant matter. Atmospheric pressure at sea level is 14.7 pounds per square inch, which is the same as 760 millimeters of mercury (Hg). In embodiments, the heat chamber vessel interior is maintained at a pressure that is below 760 mm Hg, for example, about 750 mm, about 745 mm, about 740 mm, about 735 mm, about 730 mm, about 725 mm, about 720 mm, about 715 mm, about 710 mm, about 700 mm, about 690 mm, about 680 mm, about 670 mm, about 660 mm, about 650 mm, and the like, or at a range definable by any two of the above adjacent values. Also, the heat chamber vessel interior pressure can be maintained at a positive pressure (positive relative to atmospheric pressure) that is less than about 800 mm mercury, less than about 795 mm, less than about 790 mm, less than about 785 mm, less than about 780 mm, less than about 775 mm, less than about 770 mm, less than about 765 mm, and so on.

Products of the present disclosure. The present disclosure provides oils, oil fractions, oils with a particular chemical profile, a single blend prepared by the distillation system of the present disclosure, blends of two or more fractions where each fraction is prepared by the distillation system of the present disclosure, and so on. The compositions produced by the system and methods of the present disclosure can be used in products such as, tinctures, topical lotions, spray, sublingual lozenges, suppositories, tea, e-cigarettes, and so on. The present disclosure provides compositions, formulations, solutions, and the like, capable of use with an electronic cigarette (e-cigarette). Apparatus and formulations for e-cigarettes are available. See, U.S. Pat. No. 9,254,002 of Chong and U.S. Pat. No. 8,997,753 of Li, which are incorporated herein in their entirety.

The present disclosure further provides compositions for use in lozenges (see, Meghan Emily Keck (2015) Tribological and Thermodynamic Analysis of Lozenge Decay During Oral Processing. Master's Thesis, North Carolina State Univ).

The system and methods of the present disclosure provides compositions that comprise one or more cannabinoids, one or more terpenes, or that comprise one cannabinoid and one or more terpenes, that comprise one terpene and one or more cannabinoids, or that comprise a plurality of terpenes and a plurality of cannabinoids. Also, the system and methods of the present disclosure provides compositions that consist of one or more cannabinoids, one or more terpenes, or that consist of one cannabinoid and one or more terpenes, that consist of one terpene and one or more cannabinoids, or that consist of a plurality of terpenes and a plurality of cannabinoids. These compositions, either alone or in combination with a co-administered pharmaceutical agent, can be used to provide relief from, or to treat, a variety of disorders, such as post-traumatic stress disorder (PTSD) (see, Hill et al (2018) Integrating Endocannabinoid Signaling and Cannabinoids into the Biology and Treatment of Posttraumatic Stress Disorder. Neuropsychopharmacology 43:80-102), traumatic brain injury (TBI) (see, Fernandez-Ruiz et al (2015) Cannabinoids in Neurodegenerative Disorders and Stroke/Brain Trauma: From Preclinical Models to Clinical Applications. Neurotherapeutics. 12:793-806), seizures, epilepsy, cancer, gastro-intestinal disorders, chronic pain, acute pain, opioid addiction, depression, arthritis (see, Barrie et al (2017) Endocannabinoids in arthritis: current views and perspective. Int. J. Rheum. Dis. 20:789-797), insomnia, or anxiety. Cannabinoids are used for treating anorexia, chemotherapy-induced nausea and vomiting, central pain in multiple sclerosis, neuropathic pain, cancer-related pain, and pain in diabetic peripheral neuropathy (see, Abrams (2016) integrating cannabis into clinical cancer care. Curr. Oncology. 23(S2):S8-S14: Notcutt et al (2004) Initial experiences with medicinal extracts of cannabis for chronic pain. Anaesthesia. 59:440-452).

Filtering can accomplished with paper filter, plastic polymer filler such as a Millipore® filter, micron mesh tank liner, or a cake of diatomaceous earth (Celite®), where the filler is supported by a false bottom. False bottom can be a disc with holes for allowing fluid to pass through. Mesh filters such as Spectra/Meshs® woven filters are available from, Thomas Scientific, Swedesboro, N.J. and Utah Biodiesel Supply, Clinton, Utah.

The present disclosure can include shredder, metering bin, pelletizer, cooler bin, crumbler, screen or screener, or hammer mill (reduces particulate hemp to size in range of, for example, 1.0 micrometers ($\mu$m) to 500 $\mu$m, 1.0 $\mu$m to 400 $\mu$m, 1.0 $\mu$m to 300 $\mu$m, 1.0 $\mu$m to 200 $\mu$m, 1.0 $\mu$m to 100 $\mu$m, 1.0 $\mu$m to 50 $\mu$m, 1.0 $\mu$m to 25 $\mu$m, or to a size in the range of, for example, 0.2 micrometers ($\mu$m) to 500 $\mu$m, 0.2 $\mu$m to 400 $\mu$m, 0.2 $\mu$m to 300 $\mu$m, 0.2 $\mu$m to 200 $\mu$m, 0.2 $\mu$m to 100 $\mu$m, 0.2 $\mu$m to 50 $\mu$m, 0.2 $\mu$m to 25 $\mu$m, or to a size in the range of, 2 micrometers ($\mu$m) to 500 $\mu$m, 2 $\mu$m to 400 $\mu$m, 2 $\mu$m to 300 $\mu$m, 2 $\mu$m to 200 $\mu$m, 2 $\mu$m to 100 $\mu$m, 2 $\mu$m to 50 $\mu$m, 2 $\mu$m to 25 $\mu$m, and the like). Also, the present disclosure can exclude one or more these equipments.

Reagents, chemicals, solvents, filters, and instrumentation such as spectrophotometers, mixers, condensers, distillation apparatus, and rotary evaporators, are available from, e.g., Sigma-Aldrich, St. Louis, Calif.; Life Technologies, Carlsbad, Calif.; BD Biosciences, San Jose, Calif.; EMD Millipore, Billerica, Mass.; Thomas Scientific, Swedesboro, N.J. What is available are fluorescent dyes, radioactive isotopes, electron-dense reagents, fluorettes (see, for e.g., Rozinov and Nolan (1998) Chem. Biol. 5:713-728). Falling film evaporators, rotary evaporators, distilling apparatus, and other separation equipment are available from, e.g., Thermal Kinetics, Amherst, N.Y.; Hebeler Process Solutions, Tonawanda, N.Y., Fischer Scientific, and Thomas Scientific.

Cold traps. Dewar Style Glass Cold Trap is available from Best Value Vacs, Napierville, Ill. The Dewar Style Glass Cold Trap (product code GCT-KIT) allows the user to load dry ice into the inner portion of the cold trap from the top to allow maximum condensation temperatures. This protects the vacuum pump and captures any vapors that were lost during evaporation or distillation (see, catalogue from Best Value Vacs). Another cold trap suitable for the present disclosure is Welch 1420H-14 Foreline dry ice cold trap (Cole-Parmer). According to the Cole-Parmer catalogue, dry ice traps have removable three quart well for dry ice/alcohol slurry. Liquid nitrogen cold traps efficiently trap acidic vapors and lower the vacuum pump base pressure.

Vats, kettles, and valves. What is available for system of the present disclosure are tanks with heating jackets, a cover to allow for vacuum applications, and an outlet. What is available are vacuum pans for processing food products, where boiling can be effected at reduced temperatures. What is also available are kettles, agitators, and scraper blades for use in kettles. Available valves include sanitary actuated ball valves, air-actuated valves, CIP ball valves (Clean-In-Place) (Lee Industries, Philipsburg, Pa.).

Condensers. Condenser for use in system of the present disclosure includes Graham condensers, Davies condenser, Dimroth condenser, Coil condenser, Spiral condenser, Friedrichs condenser, Allihn condenser, and so on. Graham condenser has a coolant-jacketed spiral coil running the length of the condenser serving as the vapor/condensate path. Condensers and other laboratory equipment are available from VWR, Radnor, Pa.

Filters, strainers, valves, and pumps. Filtration can be with lenticular filtration, plate and fram filtration, membrane filters, strainers (G.W. Kent, Ypsilanti, Mich.). Valves such as solonid valves and conical fermenters dual valve tap, spray rinse valve, goggle valve, vacuum distillation valve, lift plug valve, changeover valve, disc bottom outlet valve, globe valve, line blind valve, in-tank shut-off valve are available (SchuF Chemieventile Venriebs, Frankfurt, Germany; G.W. Kent, Ypsilanti, Mich.; Midwest Suppliers, St. Louis Park, Minn.). Gauges such as vacuum gauges are available (W.W. Grainger, Inc., Los Angeles, Calif.). Vacuum pumps, such as liquid ring vacuum pump, dry screw vacuum pump, rotary vane vacuum pump, scroll vacuum pump, diffusion vacuum pump, dry claw vacuum pump, PTFE diaphragm vacuum pump; DuoSeal® high vacuum pump: Vacuubrand RZ2.5® vacuum pump; are available (Busch Vacuum Pumps and Systems, Virginia Beach, Va.; Thomas Scientific, Swedesboro, N.J.). Recording thermometers are available (Thomas Scientific, Swedesboro, N.J.). Automated control of temperatures, for use in reactors, are available (M. Coughran (June 2008) Improve Batch Reactor Temperature Control. Chemical Processing. Emerson Process Management, Austin, Tex.).

Pumps suitable for system of the present disclosure can include (or exclude) centrifugal pump, twin screw pump, 3-spindle screw pump, peristaltic pump rotary vane pump, valve pump. Pumps and valves are available from, e.g., ITT Bornemann, German; SPXFLOW, Delavan, Wis.; Flomatic Corp., Glens Falls, N.Y.; CLA-VAL, Costa Mesa, Calif.; Fisher Scientific; Singer, Surrey, British Columbia). Regarding valves, a suitable hall valve is, Smith-Cooper International 8140 Series Brass Mini Ball Valve, Inline, Lever Handle, ¼" NPT Female. Needle valves can be better controlled than ball valves, and hence needle valves may be preferred for the system and methods of the present disclosure. Controller (37) is an electronic control unit for valve.

Structures of the System of the Present Disclosure

Table 1 identifies various structures of the system and methods of the present disclosure. Some of these structure numbers appear in FIG. 1 and FIG. 2.

TABLE 1

Structures of the present diclosure, including structures shown in FIG. 1 and FIG. 2

| | |
|---|---|
| 1 | Regulated radiant heat source |
| 2 | Oil bath vessel |
| 3 | Copper coil heated air tube |
| 4 | Ball valve, air induction valve (also, this can be needle valve) |
| 5 | Copper tubing connector, connects to base of heating chamber |
| 6 | Retaining nuts for connector |
| 7 | Heat seals for connector |
| 8 | Precisely controlled radiant heat source |
| 9 | Heating blanket for maintaining heat distribution around chamber |
| 10 | Heat chamber vessel, rated by plant material: Portable 5 pounds, Laboratory 10 pounds, Industrial 50 pounds |
| 11 | Copper tubing connector (connects to base of heating chamber) |
| 12 | Retaining nuts for connector |
| 13 | Vacuum seals for connector |
| 14 | Flat copper coil tubing, punctured for air flow |
| 15 | Heating vessel vacuum lid |
| 16 | Stirring rod lid hole |

TABLE 1-continued

Structures of the present diclosure, including structures shown in FIG. 1 and FIG. 2

| | |
|---|---|
| 17 | Stirring rod, fits lid hole (scales to heating vessel size). Stirring rod connects to Stirring paddle. Top of stirring rod can be looped into a handle. |
| 18 | Rotator arm, connects to rod (scales to heating vessel size). Also called, stirring paddle. |
| 19 | Structure no. 19 indicates position for a screen for holding plant material. A flat copper screen of approximately diameter of the heating chamber helps defuse incoming heated gas and keep plant material from going down into the air induction coil area. |
| 20 | Retaining nuts |
| 21 | Heat seals, stirring rod hole |
| 22 | Distillation hole (double drill for two sizes) taper insert glass tube |
| 23 | Thermometer hole |
| 24 | Thermostat |
| 25 | Heat seals |
| 26 | Heating vessel lid seal |
| 27 | Tube connector |
| 28 | Distillation tube water cooled |
| 29 | Water pump, for distillation tube |
| 30 | Ice bath tank |
| 31 | Water tubing (2), distiller to water bath |
| 32 | Tube connection with vacuum pump connection |
| 33 | Vacuum pump |
| 34 | Flask rotating connector (preferably a maximum of four flasks) |
| 35 | Collecting flasks (preferably a maximum of four flasks) |
| 36 | Controller for temperature |
| 37 | Controller for air induction valve |
| 38 | Controller for vacuum pump |
| 39 | Controller for system on |
| 40 | Rack (can be scaled for system size) |
| 41 | Tank of inert gas, preferably nitrogen gas. The tank is optional. |
| 42 | Super cold terpene trap. A Dewer cold trap is suitable for working scale model like the glass Graham condenser. Larger stainless structures are more suitable for commercial processing. |

Relationships between Components

The present disclosure provides a controlled heating chamber with agitator for plant material, air heating system for air induction module, and cold water system for condensers leading to glass globes. Condensed compounds such as terpenes and cannabinoids are captured and temporarily stored in glass globes. The glass globe section can use a single globe to pull whole plant extract or multiple globes to capture compounds vaporizing at various temperatures so that compounds have different chemical profiles. A composition with a specific, unique chemical profile may have a composition that is optimal for treating or ameliorating a specific psychological condition, or for inducing a particular mood, or for treating a specific medical disorder.

Source of inert gas and associated valves (structures 4, 37, 41) is shown in FIG. 1. Inert gas passes through copper coil heated air tube (3), where inert gas passing through tube can be heated by, for example, a surrounding electric heating clement hot water bath, hot oil bath, hot air bath, and the like. Heated air gets injects into heat chamber through the heated air tube (structure 3). Air gets injected by way of vacuum, where the vacuum pulls the precisely controlled hot air into the hear chamber vessel by allowing air to seep in from ball valve. The heat chamber assembly heat source (structure 8) is on the bottom of heat chamber. The heating blanket (structure 9) is the vertical heat source that is wrapped around the heat chamber vessel. The heat chamber (structure 10) contains organic material, where chemicals, compounds, oils, and the like in this organic material is subjected to the distillation method of the present disclosure. The stirring rod assembly (structures 17-20) maintain an even distribution of organic material across the heating vessel. Rotator arm (18) can agitate plant matter by direct physical contact, during repeated contact of rotator arm with plant matter. Rotator arm may be paddle-shaped. At the time of each repeated contact, plant matter may be shuffled about on the screen and rearranged on the screen. Alternatively at the time of each repeated contact, some or most of the plant matter can be propelled into the air, for example, for an upwards distance of up to about 2 inches, or up to about 5 inches, and the like. As another alternative, rotator arm (18) or paddle can shuffle, disrupt, and propel into the air, the plant matter by way of a wind or gust of air that is generated by the rotator arm (18).

Nature of the screen. The system, apparatus, and method of the present disclosure includes a screen. Generally, the screen includes a plurality of apertures, where each aperture defines an opening through which heated air can flow. Each of the plurality of apertures can be circular, square, rectangular, ovoid, amorphous in shape, and so on. Alternatively, the screen can take the form of a series of parallel wires that are held by a frame, for example, where each wire takes the form of a wire that stretches from one end of the screen to the opposite end of the screen. In this case, the apertures would take the form of a rectangle, where the long sides of the rectangle are hundreds or thousands of times longer than the short ends. Also, the screen can take the form of a porous "monolith," which resembles a sponge, except that pores in one face of the monolith are continuous with pores on the opposite face of the monolith, thereby allowing heated air to flow from one face of the monolith to the opposite face, and from there to contact the plant matter. Moreover, the screen can be made of metal, of plastic, or of a fabric such as that of the gauze used for bandaging wounds.

Physical nature of the plant matter. Plant matter can be freshly harvested cannabis, and retain about 100%, about 98%, about 95%, about 90%, about 85% of the moisture of the plant, as compared to immediately before harvest. Also, plant matter can be dried before extraction by the system of the present disclosure. Plant matter that is dried, can have about 5% of the moisture as compared to immediately before harvest, or about 2%, or about 1%, or about 0.5%, or about 0.2%, or about 0.1%, or about 0.05, or about 0.02%, or about 0.01%, or less than the moisture as compared to immediately before harvest. Plant matter can also have moisture levels, such as about 5-10%, about 10-20%, about 20-30%, about 30-40%, about 40-50%, about 50-60%, about 60-70%, about 70-80%, or about 20-50%, about 30-60%, about 40-70%, about 50-80%, or about 60-90%, of the moisture content, as compared to immediately before harvest. Plant matter that is either freshly harvest, or stored for several days or several weeks alter harvest but still retaining a moisture content in one of the above levels or ranges, or plant matter that is dried (as definable by one of the above values or ranges), can be chopped, minced, sliced, fragmented, or powdered, before processing with the system of the present disclosure.

The thermometer assembly (structure 24) provides readings of heat chamber temperature, thus enabling the operature to control the temperature. Ball valve (structure 4) allows for air to get heated then seeps into the heating chamber from below. Thermometer goes into tube connector (also known as, angled glass connector) (structure 27) from glass lid adaptor to condenser. Chamber thermometer sensor is optionally added just above plant material, in order to provide a chamber temperature reading and a pre-condenser temperature readings. These temperature readings can get fed into control systems for automation. Also, vacuum readings and air induction readings can get fed into control systems for automation.

In one embodiment, the system of the present disclosure has a thermometer thermocouple placed though that hole just above the plant material and glued with high-temp RTV (Room Temperature Vulcanizing). The system uses a thermometer through the lid to know the temperature inside the chamber as well as the thermometer (not thermostat) in the angled glass thing between glued-in glass adapter and glass Graham condenser. The system can include an extra thermocouple in the lid but not at the center of the lid.

The following further concerns heating blanket (structure 9). The controlled heating for the air intake are the two 36 inch by 10 inch Keeuovo heating blankets, rated at 1800 Watts on the inside and outside of the coil, and used to pre-heat the air. Hot or heated air induction is the process of pre-heating the gases going into the vat in order to pull molecule chains without lowering the chamber temperature. Here, the word "pull" means volatilize.

Heating blankets. Silicone heater is available from Keenovo (Keenovo International Group, Ltd., Shanghai, China). Thermostats can be incorporated in a heater for optimum response time and gradient control. Sensors can be integrated inside a heater, adhered to the healer surface, or installed at specific locations within the system to prevent over temperature. Maximum power density is 2.5 Watts/cm$^2$ (variable depending on different mounting methods) Kapton heater is also available from Keenovo. Kapton heater is semi-transparent, flexible and very thin with high dielectric strength, Polyimide (Kapton®) film is well suited for the manufacture of etched foil heaters, hence the name Kapton heater. Kapton heaters have low thermal mass and excellent resistance to most chemicals, and allow high power densities (8 Watts/cm$^2$) with fast and efficient thermal transfer.

Controlled air heating device. Controlled air heating device is available from Pope Scientific, Inc., Saukville, Wis. What is available is industrial oil heaters that can be used to heat vats, to a temperature greater than steam. Heating device can include two Keenovo blankets for pre-heating gasses that are pulled into the working model system, and also heating blanket (structure number 9) that gets wrapped around heating chamber. Plant heating chamber of the present disclosure has three controlled heating sources: (A) Hotplate; (B) Heating wrap (36 inches by 10 inches), and (C) Heating air induction. For heating the nitrogen (or other inert gas), after it leaves nitrogen tank, the gas passes through a tube, such as a coiled copper tube. As the gas passes through this coiled copper tube, it is heated. Heating can be via an electric heater, electric heating coils, by submersion in a hot oil bath, by exposure to a draft of heated air, and so on. Preferably, the each of these has controllable temperatures. These three heating sources, indicated above by (A), (B), and (C), are integrated into the system of the present disclosure.

Preferably, the temperatures of each of the three heating sources, indicated above by (A), (B), and (C), are controlled so that they are maintained at about the same temperature, and so that any step-wise heating or any continually rising heating, is caused to occur simultaneously at each of the hearing sources (A), (B), and (C).

Heated nitrogen would really only need to be the "induced" gas when heating chamber goes up to the 425 Fahrenheit range of plant matter combustion; which is actually variable based on how dry plant matter is or is not, how much oil is in the plant. Terpenes boil off at much lower temperatures. Some of that can be managed by the control system, where the parameters to be controlled include: temperature goal, how long to stay at temperature goal, time for temperature to go up to next temperature level, time to stay at next temperature level. Vacuum levels, humidity levels, temperatures at various points, and various sensors can be added for a more completely automated system.

Inserting plant matter into heating chamber. Heating chamber of the present disclosure can be opened, for example, for inserting plant matter, for removing extracted plant matter, or for cleaning interior of chamber. Heating chamber can be opened by way of lifting up the heating vessel vacuum lid (structure 15). Alternatively, hearing chamber of the present disclosure can be opened by using lids that are secured by bolts, where the chambers have round connectors that connect to condensing tubes. Regarding the lid (15), stirring rod, preferably with loop on top, touches the seal that is in the middle of lid (15). Vapors that contain volatilized chemicals, such as terpenes and cannabinoids, are pulled into condenser tube from a glass adaptor that, is glued to lid (15).

Controlled temperature of the system of the present disclosure. The system of the present disclosure can be operated at a single, constant heating temperature. Alternatively, the system can be operated at two different temperatures, with a stepwise transition between a first lower temperature and a second, subsequent temperature at a higher temperature. Moreover, any transition between two different temperatures can be stepwise, or it can be continuous (continuous means that, for any particular temperature, there is not any dwelling time where the temperature is substantially constant). Not counting the initial, starting temperature, the number of steps can be one step, two steps, three steps, four steps, five steps, six steps, seven steps, eight steps, nine steps, 10 steps, 11 steps, 12 steps, 13 steps, 14 steps, 15 steps, 16 steps, 17 steps, 18 steps, 19 steps, or 20 steps or more. Preferably, for any pair of adjacent steps, the first temperature is lower and the next step is at a higher temperature.

The tube connector (or tube joint) (structure 27) connects the heat chamber to distillation tube. The distillation tube (structure 28) requires the ice bath (structure 30) to be filled with ice and water. The water pump (structure 29) is turned on, and connecting the tubing (structure 31) for water flow. The vacuum pump connection (or joint) (structure 32) connects the vacuum pump (structure 33) and the flask rotator (structure 34). The collection flasks (structure 35) connect to the rotator (flask rotating connector) (structure 34).

When in operation, the heat chamber applies controlled heat to the organic material, where the controlled heat provides the release of organic compounds that vaporize at various temperatures. Subsequently, the vaporized organic compounds condense and the oil vapors are condensed to form an oil. Cooling and condensing takes place in the water-cooled distillation tube, where the distillate enters the glass globes for collecting and for temporary storage. The present disclosure provides a system and methods for collecting specific compositions having an associated chemical profile.

Each chemical profile is associated with a specific temperature, or is associated with a specific temperature range, where heating at that specific temperature (or where heating somewhere within that specific temperature range) results in collection in one of the glass globes of an oil composition with that particular chemical profile. The following example can be used to define a given chemical profile. All of the organic chemicals that are collected in a globe can comprise oils, organic chemicals that are not oils, and volatilizable minerals, for example. For this example, all of the organic chemicals that are cannabinoids and terpenes can have a weight that is set at 100 percent (100%). In this example, some of the organic chemicals may account for about 25% of this weight, while other organic chemicals may account for 8% of this weight, and other organic chemicals may account for only 0.2% of this weight. To continue with this example, the "chemical profile" can be defined by the list of all of the cannabinoids and terpenes, or alternatively, the "chemical profile" can be defined by a list of all of the cannabinoids and terpenes that make up at least 2% of the total weight of the collected terpenes and cannabinoids (while not including cannabinoids and terpenes that constitute less than 2% of the total weight of the collected terpenes and cannabinoids). In various definitions of "chemical profile," this set point can be, "at least 0.05%," "at least 0.1%," "at least 0.2%," "at least 0.5%," "at least 1%," "at least 2%," "at least 5%," "at least 10%," and so on.

A scale model of the system of the present disclosure can be marketed as a home use version. The heat chamber and heat chamber lid need to have holes drilled in order to accommodate vacuum gauge, stirring system and condenser connectors. The copper coil, both flat punctured and coils can be custom-made. Components can be assembled in a strictly defined order, or alternatively, in any logical order.

An industrial scale model, kettles and cookers for use in heating and agitating can be engineered based on the inventor's scale design in order to maintain vacuum. The scale model for home use, and the industrial scale model use vacuum and do not use any applied pressure for driving volatilized compounds out of the heating chamber to the condenser.

Steps for operating the system of the present disclosure. Organic matter is placed in the heat chamber. The organic matter can be dried cannabis, or dried cannabis that is chopped. The organic matter can be moist cannabis, that is, freshly picked cannabis or freshly picked cannabis that has been stored in a closed bag in a refrigerator. Also, the organic matter can be moist cannabis that has been chopped. The heat source is activated and the temperature set. The vacuum pump is activated and the cold water pump activated. Collection flasks are rotated as needed, to separate the output product. In contrast, if the goal is to collect only one fraction (instead of multiple fractions, acquired with heating at a different temperature), then only one collection flask may be used, if only one fraction is desired, this fraction can include all of the volatilized organic compounds that have been collected in the condenser. As an alternative to collecting all of the volatilized organic compounds, the single collected fraction can take the form of a "cut" of volatilized organic compounds that is produced at a specific temperature or specific temperature range (where organic compounds volatilized at lower temperatures are discarded). To repeat, what can be collected is a "whole plant extract" or, alternatively, a "cut" of all of the volatilized organic chemicals.

Collecting different "cuts" in different flasks can be controlled by opening or closing valves or stopcocks, or using pinchclamps on rubber connector hoses, or by manually attaching or detaching flasks from apparatus that comprises the distiller tube.

Lipids, waxes, terpenes, and cannabinoids. Lipids, such as fatty acids, and waxes, vaporize at lower temperatures. Where product contains more lipids and waxes, the extract turns the product form what is referred to as "shatter" into what is referred to as a "wax." The term "shatter" means that the substance breaks apart when snapped. The oil is coagulated with long chain molecules, where the result is that the composition acts like a plastic and acquires plastic-like attributes. A disadvantage of lipids and waxes is that the waxy extract melts away too easily, and becomes a melted mess during processing, where the melted mess has the disadvantage where it cannot be held in parchment paper. In contrast, "shatter" can easily he handled (transferred, stored) on parchment paper. Chlorophyll is disadvantageous for the compositions of the present disclosure. Chlorophyll makes oils, e.g., oils containing terpenes and cannabinoids, dark colored, does not add any medicinal properties to the oil, and results in an undesired "grassy-like" flavor.

Heavier compounds, mostly cannabinoids, get trapped in the globes. Terpenes get caught in the frozen terpene trap. Heavier compounds might, need the flow of inert gas, such as nitrogen, to enable heated air induction to allow for hotter than combustion fractional-distillation, without burning the plant matter. Temperatures of vaporization are as follows. Alpha-Pinene vaporizes at 311 degrees F. (155 degrees C.). Myrcene vaporizes at 332 degrees F. (167 degrees C.). Limonene vaporizes at 348 degrees F (176 degrees C.). Caryophyllene vaporizes at 266 degrees F. (130 degrees C.). Linalool vaporizes at 388 degrees F. (198 degrees C.). Humulene vaporizes at 222 degrees F. (106 degrees C.). Ocimene vaporizes at 122 degrees F. (50 degrees C.). Terpinolene vaporizes at 366 degrees F. (186 degrees C.). Chromatographic methods for identifying terpenes, and lists of cannabinoids and of terpenes are provided by U.S. Pat. Public. No 2015/0080265 of Elzinga, which is incorporated herein by reference in its entirety. Methods for quantifying and identifying cannabinoids are available (Sanchez-Gonzalez (2018) J. Chromatography. 1550:8-20; Citti (2018) Phytochem. Anal. 29:144-155; Nakahara (1985) J. Analyt Toxicol. 9:121-124).

Vaporization temperatures and temperature ranges for various cannabinoids, are shown below. THCA 248 degrees C. (range 140-257). CBDA 266 degrees F. (range 176-275). CBCA 284 degrees F. (212-293). THC delta-9, 311 degrees F. boiling point. CBD 329 degrees F. (range 320-356). THC delta-8, 347 degrees F. (boiling point 351 degrees F.). CBN 365 degrees F. boiling point. CBE 383 degree F. THCV 4.28 degrees F. boiling point. CBC 428 degrees F. boiling point.

Cannabinoids from cannabis sativa include tetrahydrocannabinolic acid (THCA), cannabidiolic acid (CBDA), and cannabigerolic acid (CBGA), tetrahydroccannabinoid (CBD), cannabichromene (CBC), cannabigerol (CBG), delta-9-tetrahydrocannabinol (delta-9-THC), and cannabinol (CBN) (see, Appendino et al (2008) J. Nat. Prod. 71:1427-1430). Regarding delta-8-THC, an origin of delta-8-tetrahydrocannabinol (delta-8-THC) is described (Owens et al. (1981) Clin. Chem. 27:619-624).

Exemplary temperature ranges for operating heating chamber of the present disclosure. Heating chamber temperature can start out at room temperature, e.g., 23 degrees C., and then the temperature can be raised, either stepwise gradient or in a continual gradient. For the temperatures between room temperature to about 200 degrees Fahrenheit, compounds that are volatilized can be collected, in a globe (collecting flask (35)), and then discarded. Then, temperature can be raised where, at this raised temperature, desired terpenes and cannabinoids that, are volatilized in this lower temperature range are collected in a globe. For example, caryophyllene (266 degrees F.), humulene (222 degrees F.), THCA (248 degrees F.), CBDA (266 degrees F.), and CBCA (284 degrees F.), are all volatilized in a lower temperature range, and can be collected together in one fraction. All of these terpenes and cannabinoids can be collected with use of the system at a lower temperature ranges, for example, where the heat chamber transitions in a gradient, from about 220 degrees C. to about 285 degrees C.

To given another example of a collected fraction of the present disclosure, alpha-pinene (311 degrees F.), myrcene (332 degrees F.), limonene (348 degrees F.), linalool (388 degrees F.), and terpinolene (366 degrees F.), CBN (365 degrees F.), CBD (329 degrees F.), THC delta-9 (311 degrees F.). and TCH delta-8 (347 degrees F.), can be collected with use of the system at a higher temperature range, such as a higher temperature range where the heat chamber transitions in a gradient from about 311 to 388 degrees C. Chemicals that volatilize at lower temperatures can be excluded and chemicals that volatilize at higher temperatures can also be excluded. Moreover, the product that is collected in globe is free of solvents such as ethanol, propanol, benzene, acetone, and is also free from lipids that are sometimes used as solvents, such as lipids that take the form of a vegetable oil (soy oil, corn oil, safflower oil, peanut oil, and so on).

Temperature ranges for operating in a predetermined temperature gradient, include about 120 degrees F. to about 150 degrees F., about 120-170, about 120-180, about 120-200, about 120-220, about 120-240, about 120-260, about 120-280, about 120-300, about 120-320, about 120-340, about 120-360, about 120-380, about 120-390 degrees F., and so on.

Temperature ranges for operating in a predetermined temperature gradient, include about 160 degrees F. to about 150 degrees F., about 160-170, about 160-180, about 160-200, about 160-220, about 160-240, about 160-260, about 160-280, about 160-300, about 160-320, about 160-340, about 160-360, about 160-380, about 160-390 degrees F., and so on.

Temperature ranges for operating in a predetermined temperature gradient, include about 180-200, about 180-220, about 180-240, about 180-260, about 180-280, about 180-300, about 180-320, about 180-340, about 180-360, about 180-380, about 180-390 degrees F., and so on.

Temperature ranges for operating in a predetermined temperature gradient, include about 200-240, about 200-260, about 200-280, about 200-300, about 200-320, about 200-340, about 200-360, about 200-380, about 200-390 degrees F., and so on.

Temperature ranges for operating in a predetermined temperature gradient, include about 220-240, about 220-260, about 220-280, about 220-300, about 220-320, about 220-340, about 220-360, about 220-380, about 220-390 degrees F., and so on.

In exclusionary embodiments, what can be excluded is any system, apparatus, or method, that operates within one of the above temperature ranges.

The present disclosure provides systems, reagents, and methods, that result in a composition or compositions that contain both cannabinoids and terpenes. Preferably, the composition provides an entourage effect. The term "entourage effect" refers to the influence of the combination of cannabinoids and terpenes that results in synergic effects on physiology it is recognized that, "[t]his type of synergism may play a role in the widely held . . . view that in some cases plants are better drugs than the natural products isolated from them. Support derives from studies in which cannabis extracts demonstrated effects two to four times greater than THC" (Russo (2011) Brit. J. Pharmacol. 163: 1344-1364). Moreover, it is recognized that cannabis produces its medical effects, "by virtue of the concentration and balance of various active ingredients, especially the cannabinoids . . . but also . . . a wide range of terpenoids and flavonoids" (Corral (2001) J. Cannabis Therapeutics, vol. 1, issue 3.4).

Exclusionary Embodiments

In low temperature "about" embodiments, what can be excluded is any system, device, or method, where plant matter or any other substance is extracted at a temperature that is about minus 70 degrees C., about minus 60 degrees C., about minus 50 degrees C., about minus 40 degrees C., about minus 30 degrees C., about minus 20 degrees C., about minus 10 degrees C., about zero degrees C., about 10 degrees C., about 20 degrees C., about 30 degrees C., about 40 degrees C., about 50 degrees C., about 60 degrees C., about 70 degrees C., about 80 degrees C., about 90 degrees C., about 100 degrees C., about 120 degrees C., about 140 degrees C., about 160 degrees C., about 180 degrees C., about 200 degrees C., and so on.

In low temperature "less than" embodiments, what can be excluded is any system, device, or method, where plant matter or any other substance is extracted at a temperature that is less than about minus 50 degrees C., about minus 40 degrees C., about minus 30 degrees C., about minus 20 degrees C., about minus 10 degrees C., about zero degrees C., about 10 degrees C., about 20 degrees C., about 30 degrees C., about 40 degrees C., about 50 degrees C., about 60 degrees C., about 70 degrees C., about 80 degrees C., about 90 degrees C., about 100 degrees C., about 120 degrees C., about 140 degrees C., about 160 degrees C., about 180 degrees C., about 200 degrees C., and so on.

In "about embodiments" what can be excluded is any system, device, or method, where plant matter or any other substance is extracted at a temperature is about 250 degrees F. (121 degrees C.), 260 degrees F. (127 degrees C.), 270 degrees F. (132 degrees C.), 280 degrees F. (138 degrees C.), 290 degrees F. (143 degrees C.), 300 degrees F. (149 degrees C.), 310 degrees F. (154 degrees C.), 320 degrees F. (160 degrees C.), 330 degrees F. (166 degrees C.), 340 degrees F. (171 degrees C.), 350 degrees F. (177 degrees C.), 360 degrees F. (182 degrees C.), 370 degrees F. (188 degrees C.), 380 degrees F. (193 degrees C.), 390 degrees F. (199 degrees C.), 400 degrees F. (204 degrees C.), and so on.

In "greater than about" embodiments, what can be excluded is any system, device, or method, where plant matter or any other substance is extracted at a temperature that is greater than about 250 degrees F. (121 degrees C.), 260 degrees F. (127 degrees C.), 270 degrees F. (132 degrees C.), 280 degrees F. (138 degrees C.), 290 degrees F. (143 degrees C.), 300 degrees F. (149 degrees C.), 310 degrees F. (154 degrees C.), 320 degrees F. (160 degrees C.), 330 degrees F. (166 degrees C.), 340 degrees F. (171 degrees C.), 350 degrees F. (177 degrees C.), 360 degrees F. (182 degrees C.), 370 degrees F. (188 degrees C.), 380 degrees F. (193 degrees C.), 390 degrees F. (199 degrees C.), 400 degrees F. (204 degrees C.), and so on.

In "lesser than about" embodiments, what can be excluded is any system, device, or method, where plant matter or any other substance is extracted at a temperature that is lesser than about 250 degrees F. (121 degrees C.), 260 degrees F. (127 degrees C.), 270 degrees F. (132 degrees C.), 280 degrees F. (138 degrees C.), 290 degrees F. (143 degrees C.), 300 degrees F. (149 degrees C.), 310 degrees F. (154 degrees C.), 320 degrees F. (160 degrees C.), 330 degrees F. (166 degrees C.), 340 degrees F. (171 degrees C.), 350 degrees F. (177 degrees C.), 360 degrees F. (182 degrees C.), 370 degrees F. (188 degrees C.), 380 degrees F. (193 degrees C.), 390 degrees F. (199 degrees C.), 400 degrees F. (204 degrees C.), and so on.

Pesticide weight of any prepared oil, solution, extract, distillate, paste, or grease, of the present, disclosure can be under 10 picograms (pg)/kg, under 20 pg/kg, under 40 pg/kg, under 60 pg/kg; under 100 pg/kg, under 200 pg/kg, under: 400 pg/kg, under 800 pg/kg, under 1000 pg/kg, under 10 nanograms (ng)/kg, under 20 ng/kg, under 40 ng/kg, under 60 ng/kg, under 80 ng/kg, under 100 ng/kg, under 200 ng/kg, under 400 ng/kg, under 600 ng/kg, under 800 ng/kg, under 1 micrograms/kg, under 2 micrograms/kg, under 4 micrograms/kg, under 6 micrograms/kg, under 8 micrograms/kg, under 10 micrograms/kg, under 20 micrograms/kg, under 40 micrograms/kg, under 60 micrograms/kg, under 80 micrograms/kg, under 100 micrograms/kg, under 0.2 mg/kg, under 0.4 mg/kg, under 0.6 mg/kg, under 0.8 mg/kg, under 1.0 mg/kg, under 2 mg/kg, under 4 mg/kg, under 6 mg/kg, under 8 mg/kg, under 10 mg/kg, under 20 mg/kg, under 40 mg/kg, under 60 mg/kg, under 80 mg/kg, under 100 mg/kg, under 200 mg/kg, under 400 mg/kg, under 600 mg/kg, under 800 mg/kg, under 1,000 mg/kg, and so on.

Pesticides include, Aldicarb, Abamectin, Azoxystrobin, Bifenazate, Boscalid, Bifenazate, Bifenthrin, Carbaryl, Cypermetrin, Cyflutrin, Chlofenapry, Chlorpyrifos, Captan, Dimethomorph, Diazinon, Diaminozide, Etoxazole, Fenhexamide, Fenoxycarb, Fenpyroximate, Flonicamid, Fludooxonil, Hexythiazox, Imidacloprid, Myclobutanil, Malathion, Paclobutrazole (Bonzi), Piperonyl butoxide, Pyrethrins, Propiconazole, Permetrin, Spinosad, Spinetoram, Spirotetramat, Spiromesifen, Tebuconazole, Thiamethoxam, and Trifloxystrobin.

Degrees of Purification Purification relative to pesticides. In embodiments, the present disclosure provides a product as collected in collecting flask (35), where the product is enriched in terpenes and depleted in pesticides, enriched in cannabinoid and depleted in pesticides, enriched in a particular terpene and depleted in a particular pesticide, enriched in a particular cannabinoid and depleted in a particular pesticide.

Purification relative to waxes. In embodiments, the present disclosure provides a product as collected in collecting flask (35), where the product is enriched in terpenes and depleted in waxes, enriched in cannabinoids and depleted in waxes, enriched in a particular terpene and depleted in a particular wax, enriched in a particular cannabinoid and depleted in a particular wax.

Purification relative to chlorophyll. In embodiments, the present disclosure provides a product as collected in collecting flask (35), where the product is enriched in terpenes and depleted in chlorophyll, enriched in cannabinoids and depleted in chlorophyll, enriched in a particular terpene and depleted in chlorophyll, enriched in a particular cannabinoid and depleted in chlorophyll.

Purification relative to triglycerides. In embodiments, the present disclosure provides a product as collected in collecting flask (35), where the product is enriched in terpenes and depleted in triglycerides, enriched in cannabinoids and depleted in triglycerides, enriched in a particular terpene and depleted in a particular triglyceride, enriched in a particular cannabinoid and depicted in a particular triglyceride.

Purification relative to diglycerides. In embodiments, the present disclosure provides a product as collected in collecting flask (35), where the product is enriched in terpenes and depleted in diglycerides, enriched in cannabinoids and depleted in diglycerides, enriched in a particular terpene and depleted in a particular diglyceride, enriched in a particular cannabinoid and depleted in a particular diglyceride.

Assessing degree of purification. Degree of purification can be assessed by analysis of the starting material (plant matter immediately prior to processing by system of the present disclosure) and condensed compounds in collecting flask (35), where the desired condensed compounds result from a method where a "cut" is used in the procedure involving heat gradient-induced volatilization. A collection "cut" can take the following non-limiting example. First, heating heat chamber vessel is heated at a low temperature, where volatilized chemicals are eventually condensed and collected in one collection flask, followed by increasing the temperature to a moderate temperature with collection of volatilized chemicals that are eventually condensed and collected in another collection flask, and finally, optionally heated at a high temperature where volatilized chemicals are eventually collected in still another collection flask. In this non-limiting example, the volatilized chemicals derived from the moderate temperature heat chamber vessel can be called the "cut." Quantitative analysis and qualitative analysis of desired chemicals (e.g., terpenes, cannabinoids) and undesired chemicals (e.g., waxes, triglycerides, diglycerides, chlorophyll) irons analysis of the starting material (plant matter that is to be placed on screen (19)) and the material in collecting flask (35), provide numbers that can be used to make a calculation.

The numbers used to make the calculation are "first ratio" and "second ratio." The calculation makes use of the "first ratio" of [milligrams desired chemical in plant matter]/[milligrams of undesired chemical in plant matter]. Also, the calculation makes use of the "second ratio" of [milligrams of desired chemical in collecting flask]/[milligrams undesired chemical in collecting flask]. Degree of purification is assessed by: Degree of Purification Factor=[Second ratio (flask analysis)]/[First ratio (plant matter analysis)]. Thus, if the operator is faced with a choice of keeping a substance in a $1^{st}$ collection flask, a $2^{nd}$ collection flask, a $3^{rd}$ collection flask, or a $4^{th}$ collection flask, and where the analytical data show that the substance in the $3^{rd}$ collection flask has the greatest Degree of Purification Factor, then the operator should choose to keep the substance from the $3^{rd}$ collection flask, and optionally discard the substances in the other flasks.

In embodiments, the system, apparatus, and method of the present disclosure provides a substance or composition that is characterized by a Degree of Purification Factor of at least 1.2, at least 1.4, at least 1.6, at least 1.8, at least 2.0, at least 2.2, at least 2.4, at least 2.6, at least 2.8, at least 3.0, at least 3.5, at least 4.0, at least 4.5, at least 5.0, at least 5.5, at least 6.0, and so on.

The present invention is not to be limited by compositions, reagents, methods, diagnostics, laboratory data, and the like, of the present disclosure. Also, the present invention is not be limited by any preferred embodiments that are disclosed herein.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that, one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

As one skilled in the art would recognize as necessary or best-suited for performance of the methods of the invention, a computer system or machines of the invention include one or more processors (e.g., a central processing unit (CPU) a graphics processing unit (GPU) or both), a main memory and a static memory, which communicate with each other via a bus.

A processor may be provided by one or more processors including, for example, one or more of a single core or multi-core processor (e.g., AMD Phenom II X2, Intel Core Duo, AMD Phenom II X4, Intel Core i5, Intel Core i& Extreme Edition 980X, or Intel Xeon E7-2820).

An I/O mechanism may include a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), an accelerometer, a microphone, a cellular radio frequency antenna, and a network interface device (e.g., a network interface card (NIC), Wi-Fi card, cellular modem, data jack, Ethernet port, modem rack, HDMI port, mini-HDMI port, USB port), touchscreen (e.g., CRT, LCD, LED, AMOLED, Super AMOLED), pointing device, trackpad, light (e.g., LED), light/image projection device, or a combination thereof.

Memory according to the invention refers to a non-transitory memory which is provided by one or more tangible devices which preferably include one or more machine-readable medium on which is stored one or more sets of instructions (e.g., software) embodying any one or more of the methodologies or functions described herein. The software may also reside, completely or at least partially, within the main memory, processor, or both during execution thereof by a computer within system, the main memory and the processor also constituting machine-readable media. The software may further be transmitted or received over a network via the network interface device.

While the machine-readable medium can in an exemplary embodiment be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present invention. Memory may be, for example, one or more of a hard disk drive, solid state drive (SSD), an optical disc, flash memory, zip disk, tape drive, "cloud" storage location, or a combination thereof. In certain embodiments, a device of the invention includes a tangible, non-transitory computer readable medium for memory. Exemplary devices for use as memory include semiconductor memory devices, (e.g., EPROM, EEPROM, solid state drive (SSD), and flash memory devices e.g., SD, micro SC, SDXC, SDIO, SDHC cards); magnetic disks, (e.g., internal hard disks or removable disks); and optical disks (e.g., CD and DVD disks).

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A system for extracting and purifying chemicals from plant matter, wherein the extracting uses a flow of heated air to volatilize chemicals from the plant matter, and wherein the extracting does not use any added solvent to extract chemicals from the plant matter, and wherein the system for extracting and purifying comprises a condenser that condenses at least a portion of the volatilized chemicals, the system comprising:
   (a) A source of inert gas,
   (b) A heat chamber vessel that comprises an interior chamber region, an inside wall that defines the interior chamber region, an outside wall, a base, an upper region of the interior chamber region, wherein the upper region is capable of receiving and supporting a heat chamber vessel lid, and wherein the base of the heat chamber vessel is operably linked by copper coil tubing punctured for air flow, to a source of heated inert gas,
   (c) A conduit for transmitting the inert gas to the heat chamber vessel,
   (d) A screen that is capable of supporting plant matter and capable of allowing a flow of heated air directly against at least a portion of the supported plant matter,
   (e) A rotator arm that is operably linked with a stirring rod, wherein the rotator arm is capable of agitating any plant matter that is supported by the screen,
   (f) A distillation rube comprising a proximal terminus and a distal terminus, wherein the proximal terminus is capable of receiving a vapor arriving from heat chamber vessel, and wherein the distillation tube is capable of at least partially condensing the vapor to produce a fluid, wherein the proximal terminus of said distillation tube is operably linked with the heat chamber vessel, and wherein the distal terminus of said distillation tube is operably linked with one or more collecting flasks,
   (g) One or more collecting flasks that are operably linked with the distillation tube, wherein the one or more collecting flasks is capable of receiving and storing the fluid,
   (h) At least one source of heat, wherein the at least one source of heat comprises one, two, or all three of: (1) A heat air induction system that is capable of heating inert gas leaving said source of inert gas, (2) A radiant heat source or hot plate that is situated under the heat chamber vessel and capable of transmitting heat to said interior chamber region, and (3) A heating blanket, that is wrapped around the heat chamber vessel, and capable of transmitting heat to said interior chamber region.

2. The system of claim 1, further comprising a heating vessel lid that is capable of air-tight sealing of the heat chamber vessel, and that when said heating vessel lid is engaged in air-tight sealing of the heat chamber vessel, said heating vessel lid is capable of being removed from physical contact with the heat chamber vessel thereby allowing deposit of plant matter on said screen or allowing removal of plant matter from said screen.

3. The system of claim 1, further comprising a heating vessel lid, wherein the heating vessel lid comprises a distillation hole, and wherein the distillation hole is capable of allowing passage of a vapor from the heat chamber vessel to the distillation tube.

4. The system of claim 1, wherein said conduit for transmitting an inert gas to the heat chamber vessel comprises a tube, hose, pipe, or duct.

5. The system of claim 1 that does not comprise any solvent, excluding consideration of any naturally occurring solvent that may be comprised by the plant matter.

6. The system of claim 1 that does not comprise any solvent, excluding consideration of any naturally occurring solvent that may be comprised by the plant matter, wherein the excluded solvent is one or more of ethanol, benzene, acetone, propanol and isopropanol.

7. The system of claim 1 that does not comprise any vegetable oil, excluding consideration of any naturally occurring vegetable oil that may be comprised by the plant matter.

8. The system of claim 1 that does not comprise any vegetable oil, excluding consideration of any naturally occurring vegetable oil that may be comprised by the plant matter, wherein the vegetable oil is one or more of soy oil, cottonseed oil, peanut oil, corn oil safflower oil, or sunflower oil.

9. The system of claim 1 that comprises plant matter, and wherein at least some of the plant matter is supported by the screen.

10. The system of claim 1 that comprises plant matter, and wherein at least some of the plant matter is supported by the screen, and wherein the plant matter comprises *cannabis sativa*.

11. The system of claim 1, that is capable of vaporizing terpenes and cannabinoids from plant matter at a temperature that is lower than the temperature that is needed to initiate combustion of the plant matter.

12. The system of claim 1, that is capable of heating the inert gas prior to passage of the inert gas into the heat chamber vessel, thereby preventing the inert gas from cooling the atmosphere inside heat chamber vessel.

13. The system of claim 1, wherein the heat chamber vessel comprises an interior atmosphere, wherein the system is capable of heating the inert gas prior to passage of the inert gas into the heat chamber vessel, thereby preventing the inert gas from cooling the atmosphere inside the heat chamber vessel.

14. The system of claim 1, wherein the heat chamber vessel interior has an atmospheric pressure, and wherein the atmospheric pressure is maintained at or below 760 millimeters of mercury.

15. A method for extracting and purifying chemicals from plant matter, the method comprising the steps of:
(i) Providing a flow of a heated inert gas to a heat chamber vessel, wherein the heat chamber vessel is closed to an external environment by a lid that comprises a distillation hole, wherein, the heat chamber vessel comprises a base region that comprises an inlet, a copper coil tubing punctured for air flow, an upper region, and a screen, wherein the heated inert gas is introduced at the inlet in the base region, wherein the screen is situated above the base region and below the upper region and wherein plant matter is residing on or dispersed on the screen,
(ii) Allowing the flow of healed inert gas to rise from the base region and pass through the screen, and pass through the plant matter, thereby extracting and volatilizing volatile chemicals from the plant matter, resulting in a chemical-rich vapor,
(iii) Drawing the chemical-rich vapor through the distillation hole, wherein the distillation hole is operably linked with a distillation tube, wherein the distillation tube capable of being cooled with cold water,
(iv) Cooling the distillation tube with the cold water, thereby condensing at least some of the chemicals in the chemical-rich vapor, and
(v) Collecting the condensed chemicals in at least one collecting flask, wherein the method does not involve any contacting of a liquid solvent with the plant matter, does not involve any contacting of a vegetable oil with the plant matter, does not involve any extracting of chemicals from the plant matter with a liquid solvent, and does not involve any extracting of chemicals from the plant matter with any vegetable oil.

16. The method of claim 15, wherein the plant matter is *cannabis sativa*.

17. The method of claim 15, wherein the volatile chemicals from the plant matter comprise terpenes and cannabinoids.

18. The method of claim 15, further comprising agitating the plant matter with a rotator arm, wherein the rotator arm is operably linked to a stirring rod, further comprising driving the stirring rod with angular momentum, either manually or with a motor, thereby resulting in rotation of the rotator arm.

19. The method of claim 15, wherein the heat chamber vessel comprises a base, further comprising: (1) Heating the heat chamber vessel with a heating blanket, (2) Heating the heat chamber vessel with a radiant heat source or hot plate, and (3) Heating the inert gas to produce a heated inert gas, wherein the heated inert gas is introduced at the base of the heat chamber vessel, and wherein the heating of the inert gas is sufficient to prevent the introduced heated inert gas from cooling down the heat chamber vessel.

20. The method of claim 15, further comprising analyzing the collected condensed chemicals, and quantifying and identifying any terpenes and cannabinoids.

21. The method of claim 15 that results in a Degree of Purification Factor of at least 1.5, where the Degree of Purification Factor is calculated by quantitative analysis of the sum of at least 90% of all terpenes and by quantitative analysis of the sum of at least 90% of all waxes, and where quantitative analysis is performed on the starting material (plant matter) and on the product (composition in collection flask).

* * * * *